US010660635B2

(12) United States Patent
Munday

(10) Patent No.: US 10,660,635 B2
(45) Date of Patent: May 26, 2020

(54) APPARATUS AND METHOD FOR CLOSING A SURGICAL SITE

(71) Applicant: George Swope Munday, Danville, KY (US)

(72) Inventor: George Swope Munday, Danville, KY (US)

(*) Notice: Subject to any disclaimer, the term of this patent is extended or adjusted under 35 U.S.C. 154(b) by 0 days.

(21) Appl. No.: 16/377,600

(22) Filed: Apr. 8, 2019

(65) Prior Publication Data

US 2019/0350580 A1    Nov. 21, 2019

Related U.S. Application Data

(63) Continuation of application No. PCT/US2018/045517, filed on Aug. 7, 2018.
(Continued)

(51) Int. Cl.
| | | |
|---|---|---|
| *A61B 17/04* | (2006.01) | |
| *A61B 17/06* | (2006.01) | |
| *A61B 34/30* | (2016.01) | |
| *A61B 90/00* | (2016.01) | |
| *A61B 17/00* | (2006.01) | |

(52) U.S. Cl.
CPC ...... *A61B 17/0469* (2013.01); *A61B 17/0482* (2013.01); *A61B 17/0483* (2013.01); *A61B 17/06123* (2013.01); *A61B 34/30* (2016.02); *A61B 17/0057* (2013.01); *A61B 2017/00637* (2013.01); *A61B 2017/00663* (2013.01);
(Continued)

(58) Field of Classification Search
CPC ........ A61B 17/06114; A61B 17/06119; A61B 17/06123; A61B 17/06128; A61B 17/06133; A61B 17/06138; A61B 17/06142; A61B 17/06147; A61B 17/06152; A61B 17/06157; A61B 17/0482; A61B 17/0483; D05B 91/16; D05B 91/26; B65H 49/00; B65H 49/18; B65H 49/20; B65H 49/205; B65H 49/38; B65H 2701/533
See application file for complete search history.

(56) References Cited

U.S. PATENT DOCUMENTS

| | | | | |
|---|---|---|---|---|
| 633,404 | A | * 9/1899 | Wharburton | ........... A01K 97/06 242/138 |
| 3,901,244 | A | * 8/1975 | Schweizer | ............. A61B 17/04 606/145 |

(Continued)

FOREIGN PATENT DOCUMENTS

| | | |
|---|---|---|
| WO | 9826719 A1 | 6/1998 |
| WO | 2006050080 A2 | 5/2006 |

(Continued)

OTHER PUBLICATIONS

3CT Search Report and Written Opinion completed by the ISA/US and issued in connection with PCT/US2018/045517.

*Primary Examiner* — Martin T Ton
(74) *Attorney, Agent, or Firm* — Barnes & Thornburg, LLP

(57) ABSTRACT

A suturing device includes a clamshell body having a first side coupled to a second side by a hinge. The first side and the second side each have an end opposite the hinge. A spool is coupled to the clamshell body and rotatable relative to the clamshell body. A suture is wound around the spool. The ends of the first side and the second side may lock together to capture an end of the suture.

14 Claims, 12 Drawing Sheets

Related U.S. Application Data

(60) Provisional application No. 62/672,085, filed on May 16, 2018.

(52) U.S. Cl.
CPC ............ *A61B 2017/00876* (2013.01); *A61B 2034/302* (2016.02); *A61B 2090/036* (2016.02)

(56) References Cited

U.S. PATENT DOCUMENTS

| | | |
|---|---|---|
| D301,373 S | 5/1989 | Peters |
| 5,021,059 A | 6/1991 | Kensey et al. |
| 5,059,201 A | 10/1991 | Asnis |
| 5,089,012 A | 2/1992 | Prou |
| 5,160,339 A | 11/1992 | Chen et al. |
| 5,171,253 A | 12/1992 | Klieman |
| 5,325,868 A | 7/1994 | Kimmelstiel |
| 5,413,585 A | 5/1995 | Pagedas |
| 5,507,775 A | 4/1996 | Ger et al. |
| 5,514,159 A | 5/1996 | Matula et al. |
| 5,675,961 A | 10/1997 | Cerwin et al. |
| 5,735,877 A | 4/1998 | Pagedas |
| 5,830,157 A | 11/1998 | Foote |
| 5,911,728 A | 6/1999 | Sepetka et al. |
| 6,015,428 A | 1/2000 | Pagedas |
| 6,050,981 A | 4/2000 | Lampropoulos et al. |
| 6,066,160 A | 5/2000 | Colvin et al. |
| 6,126,677 A | 10/2000 | Ganaja et al. |
| 6,143,004 A | 11/2000 | Davis et al. |
| 6,200,329 B1 | 3/2001 | Fung et al. |
| 6,214,332 B1 | 4/2001 | Askill et al. |
| 6,293,961 B2 | 9/2001 | Schwartz et al. |
| 6,471,715 B1 | 10/2002 | Weiss |
| 6,860,895 B1 | 3/2005 | Akerfeldt et al. |
| 6,939,357 B2 | 9/2005 | Navarro et al. |
| 7,033,379 B2 | 4/2006 | Peterson |
| 7,144,412 B2 | 12/2006 | Wolf et al. |
| 7,204,841 B2 | 4/2007 | Green |
| 7,351,249 B2 | 4/2008 | Hnojewyj et al. |
| 7,407,505 B2 | 8/2008 | Sauer et al. |
| 7,468,068 B2 | 12/2008 | Kolster |
| 7,470,256 B2 | 12/2008 | Lampropoulos et al. |
| 7,520,869 B2 | 4/2009 | Lampropoulos et al. |
| 7,544,187 B2 | 6/2009 | Lampropoulos et al. |
| 7,547,296 B2 | 6/2009 | Lampropoulos et al. |
| 7,582,105 B2 | 9/2009 | Kolster |
| 9,468,435 B2 | 10/2016 | Ashland |
| 9,655,622 B2 | 5/2017 | Jonn et al. |
| 9,775,601 B2 | 10/2017 | Keating et al. |
| 2003/0204195 A1 | 10/2003 | Keane et al. |
| 2004/0133239 A1 | 7/2004 | Singhatat |
| 2004/0260344 A1 | 12/2004 | Lyons et al. |
| 2005/0033365 A1 | 2/2005 | Courage |
| 2005/0085855 A1 | 4/2005 | Forsberg |
| 2006/0058844 A1 | 3/2006 | White et al. |
| 2006/0069397 A1 | 3/2006 | Nobles et al. |
| 2006/0106418 A1 | 5/2006 | Seibold et al. |
| 2006/0106423 A1 | 5/2006 | Weisel et al. |
| 2006/0265006 A1 | 11/2006 | White et al. |
| 2007/0004991 A1 | 1/2007 | Shelton |
| 2007/0032821 A1 | 2/2007 | Chin-Chen et al. |
| 2007/0210131 A1* | 9/2007 | Yarborough ......... B65H 49/205 |
| | | 225/56 |
| 2008/0015635 A1 | 1/2008 | Olsen et al. |
| 2008/0015636 A1 | 1/2008 | Olsen et al. |
| 2008/0097479 A1 | 4/2008 | Boehlke et al. |
| 2008/0269785 A1 | 10/2008 | Lampropoulos et al. |
| 2008/0300629 A1 | 12/2008 | Surti |
| 2009/0043246 A1 | 2/2009 | Dominguez |
| 2009/0069847 A1 | 3/2009 | Hashiba et al. |
| 2009/0076546 A1 | 3/2009 | Ashley et al. |
| 2009/0143817 A1 | 6/2009 | Akerfeldt |
| 2009/0234295 A1 | 9/2009 | Lampropoulos et al. |
| 2010/0230300 A1* | 9/2010 | Hunter ............ A61B 17/06114 |
| | | 206/63.3 |
| 2013/0165954 A1 | 6/2013 | Dreyfuss et al. |
| 2015/0088195 A1 | 3/2015 | Moustafa |
| 2015/0157316 A1 | 6/2015 | Labarbera |
| 2016/0376240 A1 | 12/2016 | Bunnelle et al. |

FOREIGN PATENT DOCUMENTS

| | | |
|---|---|---|
| WO | 2008033766 A2 | 3/2008 |
| WO | 2009052509 A1 | 4/2009 |
| WO | 2009114811 A2 | 9/2009 |

\* cited by examiner

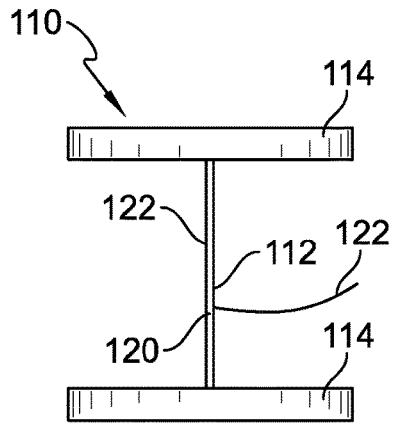
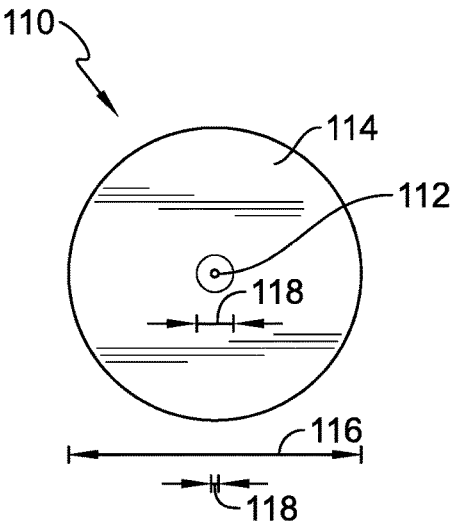
FIG. 2　　　　FIG. 3
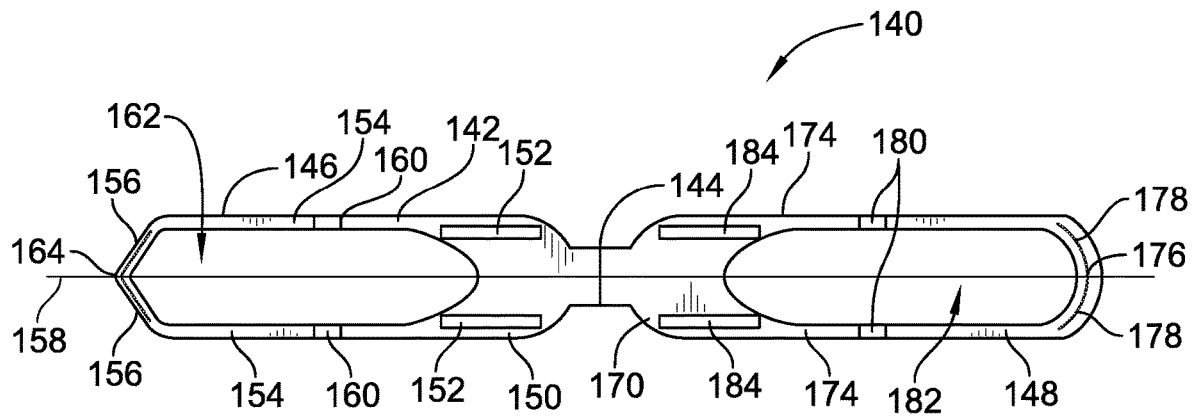
FIG. 4
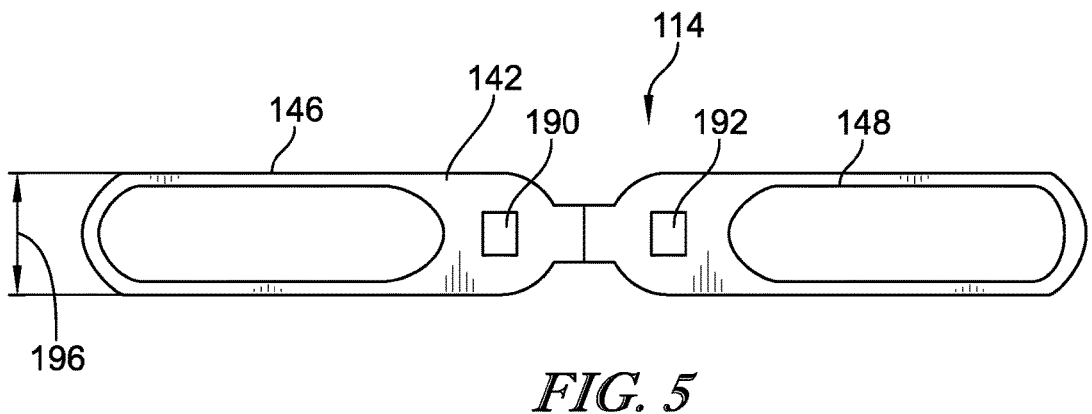
FIG. 5

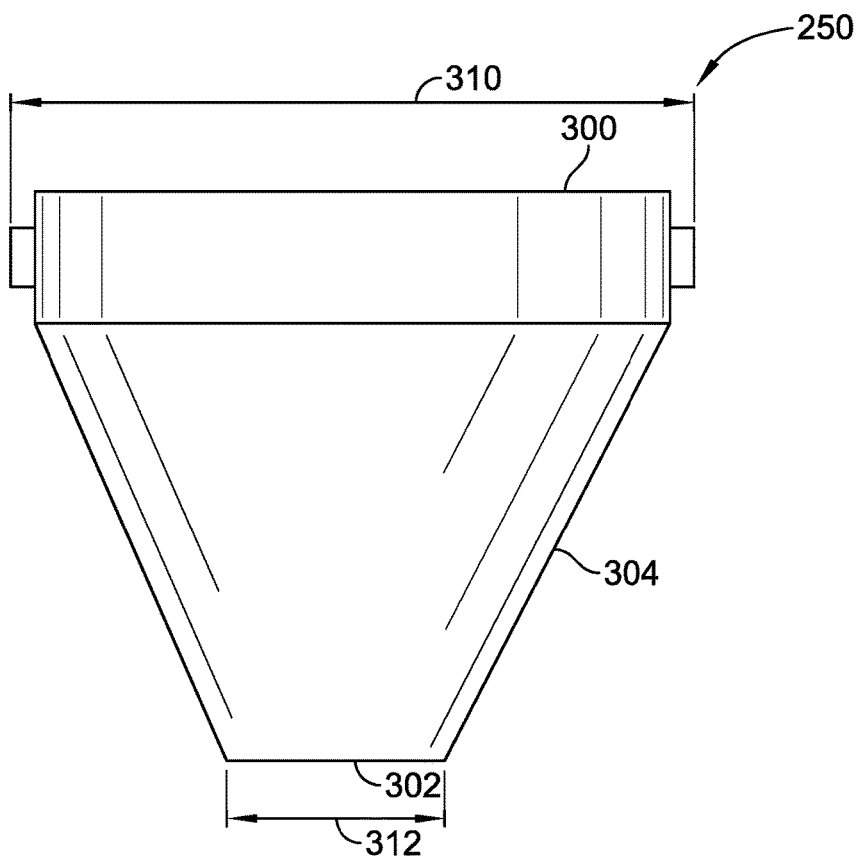
FIG. 9
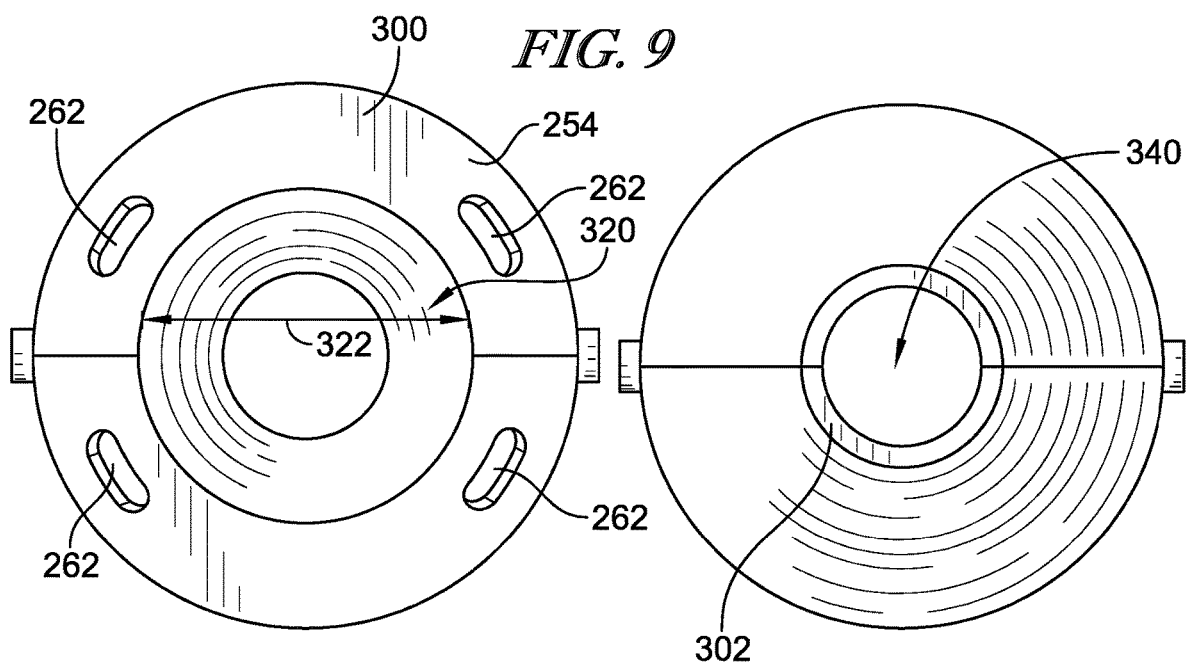
FIG. 10
FIG. 11

APPARATUS AND METHOD FOR CLOSING A SURGICAL SITE

CROSS-REFERENCE TO RELATED APPLICATIONS

This application is a continuation of international application serial No. PCT/US2018/045517, filed Aug. 7, 2018, which claims priority to U.S. Provisional Patent Application Ser. No. 62/672,085, filed May 16, 2018. The disclosures of both PCT/US2018/045517 and U.S. Provisional Application Ser. No. 62/672,085 are incorporated herein by reference in their entirety.

TECHNICAL FIELD

The present disclosure relates to surgical instruments and particularly, to an instrument and method for closing a surgical site.

BACKGROUND

The fascial closure portion of any surgical case is critical. A well preformed minimally invasive surgery can result in a complication if this final portion of the case is neglected or done poorly. Any abdominal wall defect greater than 8 mm should be accompanied by a fascial closure to reduce the risk of incisional hernia. Incisional hernias can be very costly complications. They lead to increased hospital stays; increased patient pain and suffering; and most often times an ensuing operation. Incisional hernias can also be life-treating if the bowel becomes strangulated and ischemic. The rates of incisional hernia have been alarmingly high in single incision minimally invasive techniques and have prevented such techniques from becoming more widely adapted as the standard of care.

The current technologies and devices for port site fascial closure are antiquated and require an immense amount of skill to use. Therefore, the results are not widely reproducible even in the most talented hands. The embodiments described herein will allow the integration of computer aided surgery (robotics) into the fascial closure portion of a case. As computer aided surgery continues to progress, automation will become more accepted and adopted. With automation, surgery will become safer, more uniformly reproducible and efficient. This could potentially impact overall patient outcomes, access to surgical care; and reduce overall cost by eliminating human error from the surgical suite. The disclosed embodiments will help continue the progression and widespread integration of single incision minimally invasive surgery and computer aided surgical techniques. Suture management is a problematic technical skill for robotic surgeons in general surgical cases such as ventral and incisional hernia repair Suture management is crucial during robotic surgeries of the GI tract and abdominal wall. An efficient management of suture can lower the cost of each case by reducing console and overall operating room times. Currently, when the suture is introduced into the robotic surgical field, it is unorganized and tangled. The suture is at the risk of knotting, breaking or incidentally being cut while it is being organized to begin closing a ventral defect or affixing a mesh to the anterior abdominal wall. Sometimes to avoid this issue of un-manageable suture, surgeons will reduce the length of the suture. This prevents difficulty with suture management but often contributes to multiple lengths of suture introduced by an assistant throughout the case. This practice can be time consuming. This practice can also potentially have a higher risk of a retained foreign body or incorrect counts by using multiple needles to complete one case.

SUMMARY

The present disclosure includes one or more of the features recited in the appended claims and/or the following features which, alone or in any combination, may comprise patentable subject matter.

In one aspect of the disclosed embodiments, a device for assisting in suturing the fascial tissue after an abdominal surgery is provided. The device could also be utilized during robotic intraabdominal, thoracic and pelvic surgery as a suture carriage. The device includes a clam-shell housing that retains a spool of suture. The loose end of the suture is clamped and retained at an end of the device so that the suture extends through an eyelet between the end and the spool. The device is inserted into the abdomen through a surgical port. A suture grabber is inserted through a guide ring and grabs the suture in the eyelet of the device. The grabber pulls the suture through the fascial tissue to form a first end to be tied. The grabber than grabs another portion of the suture and pulls a second end to be tied through the fascial tissue. The device and port are removed and the two ends are tied.

In another aspect of the disclosed embodiments, a suturing device includes a clamshell body having a first side coupled to a second side by a hinge. The first side and the second side each have a clamping end opposite the hinge. A slot is formed in each of the first side and the second side. The slot in the first side is aligned with the slot in the second side when the clamshell body is closed to form a cavity. A spool is included having a rod extending from an end cap. The end cap is retained in the cavity and is rotatable relative to the clamshell body. A suture is wound around the rod of the spool. The clamping ends of the first side and the second side lock together to capture an end of the suture.

In some embodiments, each of the first side and the second side may include a first slot and a second slot. The first slots of the first side and the second side may form a first cavity to retain a first end cap of the spool. The second slots of the first side and the second side may form a second cavity to retain a second end cap of the spool. The rod of the spool may extend between the first end cap and the second end cap.

In some embodiments, an eyelet may extend between the ends of the first side. The suture may be accessible through the eyelet. An eyelet may extend between the ends of the second side. The suture may be accessible through the eyelet. An eyelet may be formed between the first side and the second side when the first side and the second side are coupled together. The suture may be accessible through the eyelet.

In some embodiments, the suture may extend between the spool and the clamping end of the clamshell body. The clamshell body may be configured to be retained by a robotic arm. The clamshell body may be sized to be extended through a trocar.

In some embodiments, a guide ring may be configured to couple to a trocar. The guide ring may be configured to receive a suture grabber that grabs the suture in the clamshell body. The guide ring may include a conical sidewall extending between a first end and a second end. The conical sidewall may be sized to position around a trocar. The first end of the guide ring may include a flange having a plurality of openings. The openings may be sized to receive a suture grabber. An opening defined by the flange may be sized to position around a trocar. The guide ring may include a first half and a second half that is separable from the first half. The first half may be coupled to the second half to couple the guide ring to the trocar. A needle may be attached to an end of the suture for a hernia closure procedure.

In yet another aspect of the disclosed embodiments, a method of suturing an abdominal cavity includes inserting a spool of suture in the abdominal cavity. The method also includes capturing a first portion of the suture and removing the first portion from the abdominal cavity. The method also includes capturing a second portion of the suture and removing the second portion from the abdominal cavity. The method also includes tying the first portion to the second portion outside of the abdominal cavity.

In some embodiments, the spool may be retained in a clamshell body. The method may also include inserting the clamshell body into the abdominal cavity. The method may also include capturing the first portion of the suture in an eyelet of the clamshell body. The method may also include capturing the second portion of the suture in the eyelet of the clamshell body. The method may also include capturing the first portion of the suture and the second portion of the suture with a suture grabber. The method may also include inserting the suture grabber through an opening of a guide ring.

The embodiments described herein can also be utilized during robotic intra-abdominal, thoracic and pelvic surgery as a suture and needle carriage with immediate application in abdominal wall reconstruction and intra-corporeal anastomosis.

BRIEF DESCRIPTION OF THE DRAWINGS

The detailed description particularly refers to the accompanying figures in which:

FIG. 2 is a side elevation view of a spool of suture thread that is used with the surgical instrument;

FIG. 3 is a top plan view of the spool shown in FIG. 2;

FIG. 4 is a top plan view of the surgical instrument in an open configuration;

FIG. 5 is a bottom plan view of the surgical instrument shown in FIG. 4 in the open configuration;

FIG. 9 is a side elevation view of a guide ring in accordance with an embodiment;

FIG. 10 is a top plan view of the guide ring shown in FIG. 9;

FIG. 11 is a bottom plan view of the guide ring shown in FIG. 9;

DETAILED DESCRIPTION

Figures 1, 1A:
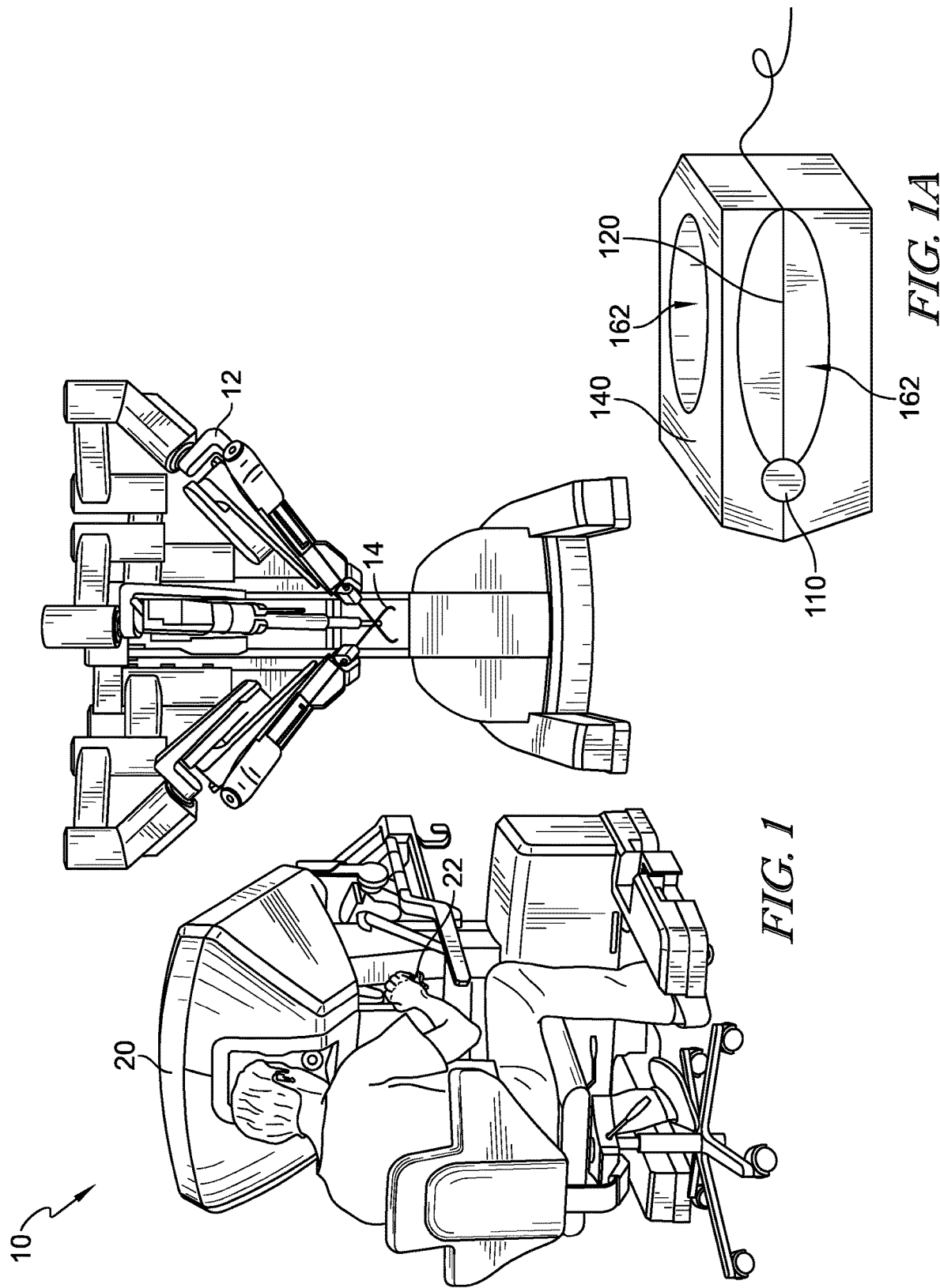
FIG. 1 is a perspective view of an automated surgical system.
FIG. 1A is a side perspective view of a surgical instrument that may be used with the automated surgical system shown in FIG. 1.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, an automated surgery system 10 includes at least one robotic arm 12 having a plurality of fingers 14 to grab surgical instruments. The robotic arm 12 is positioned at a surgical site so that the robotic arm 12 can manipulate the instruments at the surgical site. A control panel 20 includes a plurality of controls 22, e.g. a joystick, for a surgeon to manipulate the robotic arms 12 during surgery.

Referring to FIG. 1A, a suturing instrument 140 is configured to be used with the automated surgery system 10. In some embodiments, the suturing instrument 140 is used manually and held by the surgeon using a manual arm. The suturing instrument 140 is configured to retain a spool 110 of suture thread 120. The suturing instrument 140 is positioned with a surgical site under the patient's skin and tissue. The suture thread 120 is retained in an eyelet 162 of the suturing instrument 140 so that the suture thread is accessible to be grabbed by another surgical instrument, i.e. a suture passer. The suture passer is inserted into the surgical site and grabs a portion of the suture thread 120 positioned in the surgical site. The suture thread 120 is then pulled out of the surgical site with the suturing instrument 140 remaining is position in the surgical site. The suturing instrument 140 is then rotated and positioned for a second pass of the suture passer. The suture passer grabs a second portion of the suture thread 120 and pulls the second portion from the surgical site so that two ends of the suture thread 120 are positioned outside of the surgical site and a segment of the suture thread 120 between the two ends is positioned within the surgical site. The suturing instrument 140 can then be removed from the surgical site with the suture thread 120 is place. The ends of the suture thread 120 are then tied together to close the surgical site. As set forth above, the suturing instrument 140 may be operated by the automated surgery system 10 or may be operated manually by the surgeon.

Referring to FIGS. 2-3, a spool 110 includes a center post 112 and a pair of ends 114 on each end of the center post 112. Each of the ends 114 is circular so the spool 110 can roll or rotate on the ends 114. The ends 114 have a radius 116 that is greater than a radius 118 of the center post 112. The center post 112 is configured to retain a strand of suture thread 120. The strand of suture thread 120 is wound around the center post 112. A loose end 122 of the suture thread 120 extends from the center post 112 so that the loose end 122 can be grabbed to unwind the strand of suture thread 120 from the center post 112.

Referring to FIG. 4, a suturing instrument 140 is configured to retain the spool 110 so that the spool 110 can rotate with respect to the device 140 to unwind the strand of suture 120. The suturing instrument 140 includes a chassis 142 that is configured as a clamshell body. The chassis 142 is created from a single piece of polymer. The chassis 142 is designed with a hinge 144 to fold upon itself while encasing the spool 110 and locking the thread 120 in place. The chassis 142 includes a top end 146 and a bottom end 148 coupled to the top end 146 by the hinge 144. A body 150 of the top end 146 includes a pair of grooves 152 that are each configured to retain one of the ends 114 of the spool 110 so that the spool 110 rotates within the groove 152. A pair of arms 154 extends from the body 150 to an end 164 that is formed by a pair of angled arms 156 that join along a centerline 158 of the chassis 142. A stabilizing post 160 is positioned on each arm 154. An eyelet 162 is defined between the arms 154, the arms 156 and the body 150. A length of the eyelet 162 can be variable depending on the robotic arm 12 used and the best angles for fascial approximation. A body 170 of the bottom end 148 includes a pair of grooves 184 that are each configured to retain one of the ends 114 of the spool 110 so that the spool 110 rotates within the groove 184. The grooves 184 are configured to align with the grooves 152 when the chassis 142 is closed. A pair of arms 174 extends from the body 170 to an end 176 that is formed by a pair of angled arms 178 that join along the centerline 158 of the chassis 142. A stabilizing post 180 is positioned on each arm 174 and is configured to align with the stabilizing posts 160 when the chassis 142 is closed. An eyelet 182 is defined between the arms 174, the arms 178 and the body 170. A length of the eyelet 182 can be variable depending on the robotic arm 12 used and the best angles for fascial approximation.

Referring to FIG. 5, the top end 146 includes a notch 190 that is configured to receive a finger 14 of a robotic arm 12 to retain the chassis 142 on the robotic arm 12. Likewise, the bottom end 148 includes a notch 192 that receives a finger 14 of a robotic arm 12 to retain the chassis 142 on the robotic arm 12. The chassis 142 is grabbed between the fingers 14 of the robotic arm 12 so that the chassis 142 is retained between the fingers 14. The chassis 142 has a depth 196, as illustrated in FIGS. 4-5.

Figure 6:
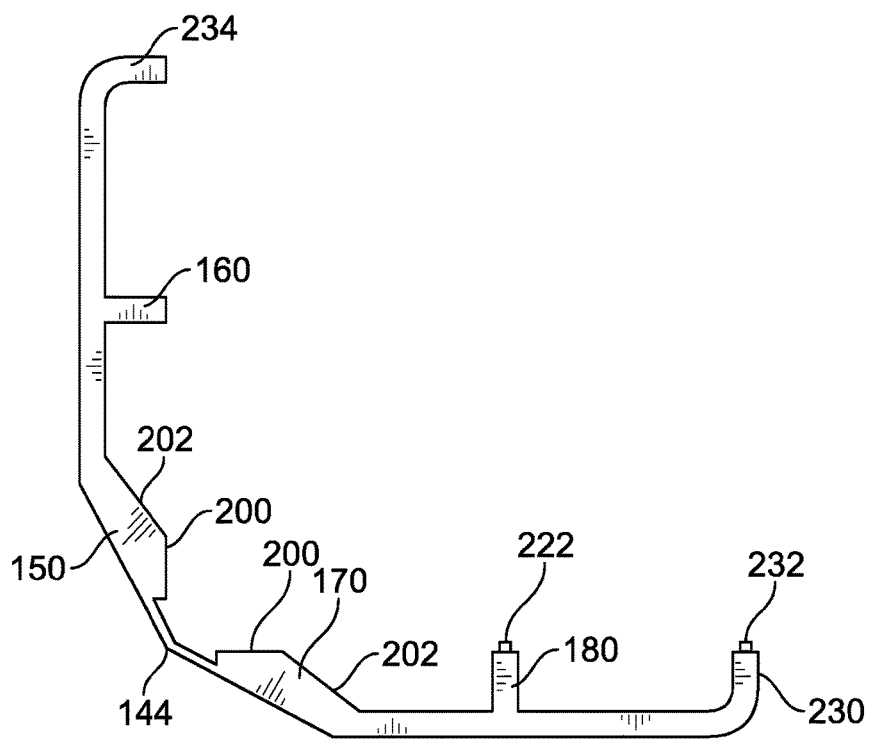
FIG. 6 is a side elevation view of the surgical instrument shown in FIG. 4 in a partially open configuration.
Figure 7:
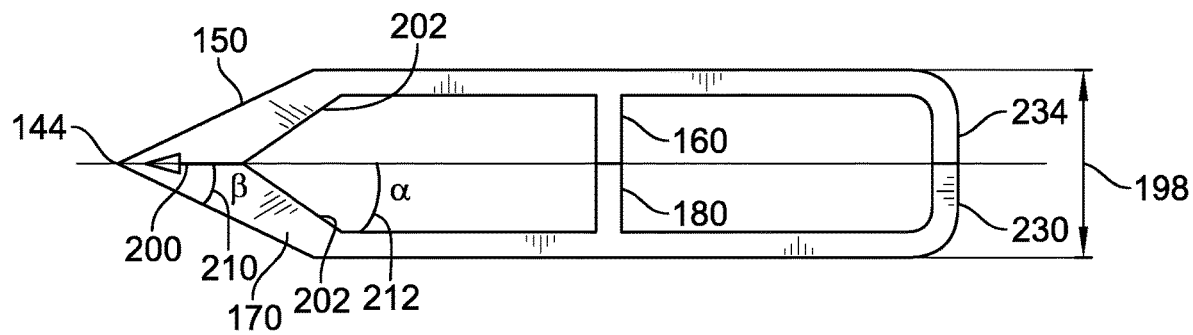
FIG. 7 is a side elevation view of the surgical instrument shown in FIG. 4 in a closed configuration.
Figure 8:
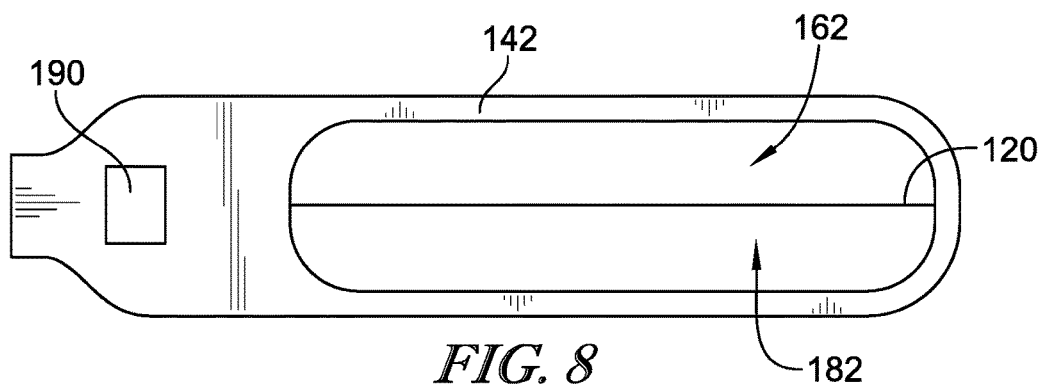
FIG. 8 is a top plan view of the surgical instrument shown in FIG. 4 is a closed configuration.

Referring to FIGS. 6-7, the bodies 150 and 170 have angled walls 200 that extend from the hinge 144. Another angled wall 202 extends from each angled wall 200. Outer walls 204 extend opposite the angled walls 200 and 202. When the chassis 142 is closed, the outer walls 204 extend at an angle 210 with respect to the centerline 158 of the chassis 142. In some embodiments, the angle 210 is approximately 25°. The angled walls 202 extend at an angle 212 relative to the centerline 158. In some embodiments, the angle 212 is approximately 35°. When closed, the chassis 142 has a height 198 that may be equal to the depth 196. The stabilizing post 180 includes a tab 222 that inserts into an opening (not shown) of the stabilizing post 160 to secure the stabilizing post 180 to the stabilizing post 160. Likewise, an end jaw 230 of the bottom end 148 includes a tab 232 that inserts into an opening (not shown) formed in an end jaw 234 of the top end 146 to secure the top end 146 to the bottom end 148. The thread 120 extends from the spool 110 positioned between the bodies 150 and 170, between the stabilizing posts 160, 180, and to the end jaws 230 and 234. The loose end 122 of the thread 120 is secured between the end jaws 230 and 234 of the chassis 142. As illustrated in FIG. 8, the thread 120 extends through the eyelets 162, 182 of the chassis 142.

The chassis 142 may be manufactured in various sizes to accommodate different robotic arm 12 and port diameters. The chassis 142 can be directly grasped by an arm (either robotic or handheld) and inserted directly through a port site that will be closed. The suture type loaded on the spool 110 can be variable to account for different surgeon preference. The suture 120 is loaded on spool and the end 122 is grasped within the end jaws 230, 234 of chassis 142. The end 122 is retained in a fixed position between the end jaws 230, 234, as shown in FIGS. 18-22. That is, FIGS. 18-22 show the suture 120 being pulled while the end 122 of the suture 120 is retained in a fixed position between the end jaws 230, 234. The eyelets 162, 182 of the chassis 142 are designed to optimize negative space while maintaining stability. This allows for ample space for a suture passer to access the suture 120. The stabilizing posts 160, 180 may be omitted if the material strength allows. If omitted the suture 120 can be accessed from all 4 sides of the chassis 142 with a suture passer. The chassis 142 may be manufactured with a needle on the end of the suture to allow intra-abdominal suturing.

Referring to FIG. 9, a guide ring 250 includes a top end 300, a bottom end 302, and a sidewall 304 extending between the top end 300 and the bottom end 302. The guide ring 250 is made from a polymer and can be disposable or re-useable. The sidewall 304 is frusto-conical in shape and narrows from a top diameter 310 at the top end 300 to a bottom diameter 312 at the bottom end 302. The guide ring 250 is sized to position around a trocar 252 (described below). The guide ring 250 is a plastic ring that is affixed to the outside of the trocar 252. Referring to FIG. 10, the top end 300 has a lip 254 that extends inward from the sidewall 304. A trocar aperture 320 is centered in the top end 300. The lip 254 extends around the trocar aperture 320. The trocar aperture 320 has a diameter 322 that is sized to be positioned around a trocar. The guide ring 250 is designed with markings for optimal suture spacing for varying sized trocars 252. The guide ring 250 can have markings that line up with the skin incision or built in magnets to auto-orient to the arm's position within the patient. The lip 254 ensures that the dermis will not be included in fascial closure. Suture passer apertures 262 are positioned on the guide ring 250 on a rim of the lip 254. In the illustrated embodiment, the guide ring 250 includes four suture passer apertures 262. The suture passer apertures 262 are sized to receive the arm of a suture passer (described below). Referring to FIG. 11, the bottom end 302 includes an exit aperture 340 that is sized to fit around the trocar 252.

Figure 12:
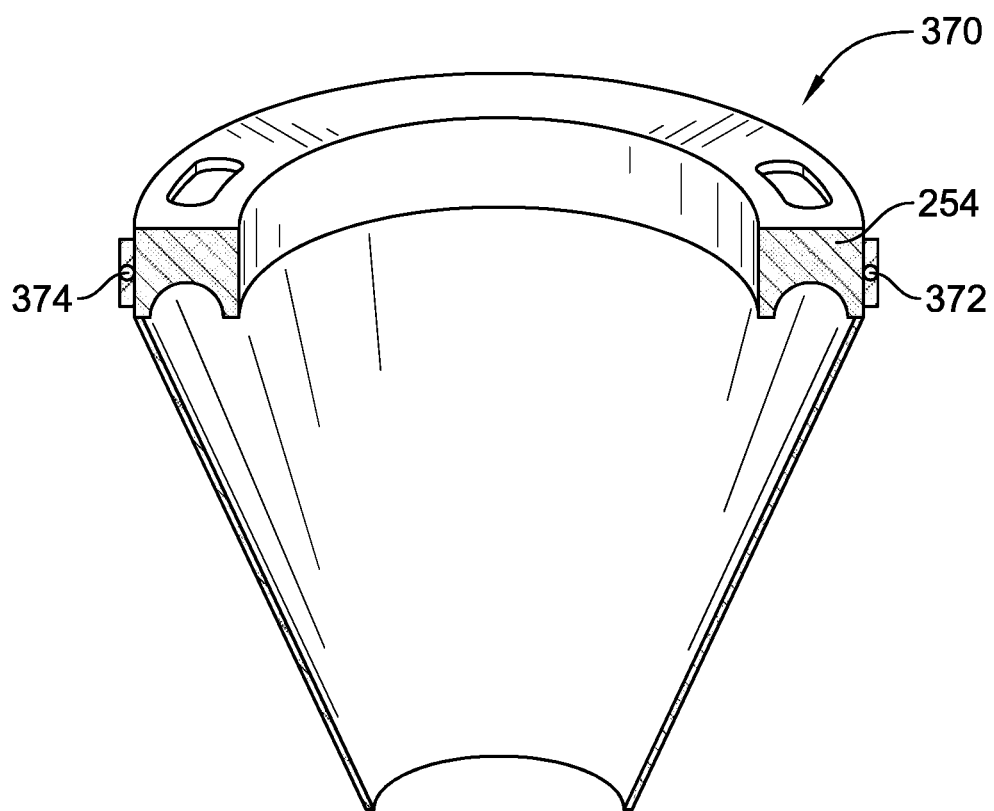
FIG. 12 is a side perspective view of a half of the guide ring shown in FIG. 9.
Figure 13:
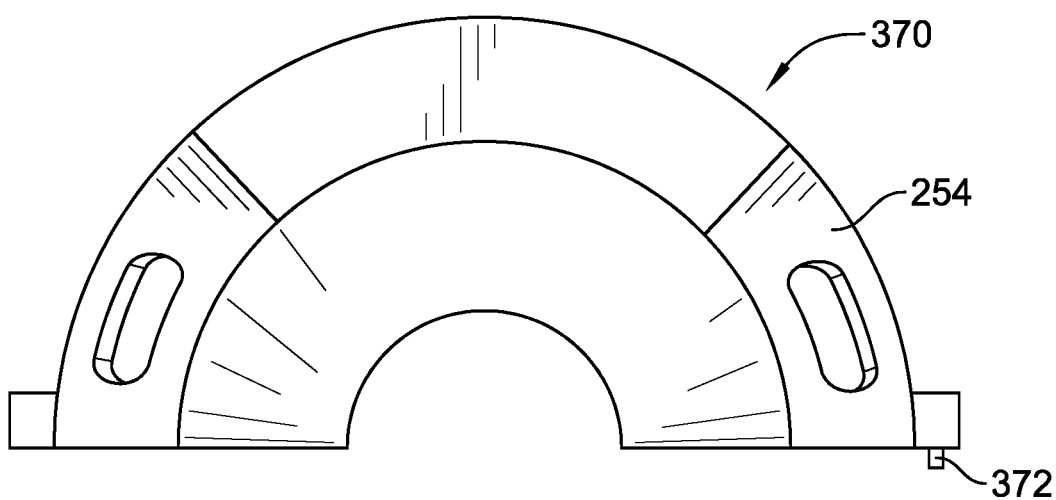
FIG. 13 is a top plan view of the guide ring half shown in FIG. 12.

As seen in FIGS. 12-13, the guide ring 250 includes two halves or hemi-guide rings 370. The hemi-guide rings 370 clip together to form the assembled guide ring 250. Each hemi-guide ring 370 includes a post 372 extending from the lip 254. Each hemi-guide ring 370 also includes an opening 374 extending into the lip 254. The post 372 of a first hemi-guide ring 370 is configured to insert into the opening 374 of a second hemi-guide ring 370, and the post 372 of the second hemi-guide ring 370 is configured to insert into the opening of the first hemi-guide ring 370 to clip the first hemi-guide ring 370 to the second hemi-guide ring 370 to form the guide ring 250. In use the hemi-guide rings 370 are clipped around the trocar 252 to position the guide ring 250 onto the trocar 252.

Figure 14:
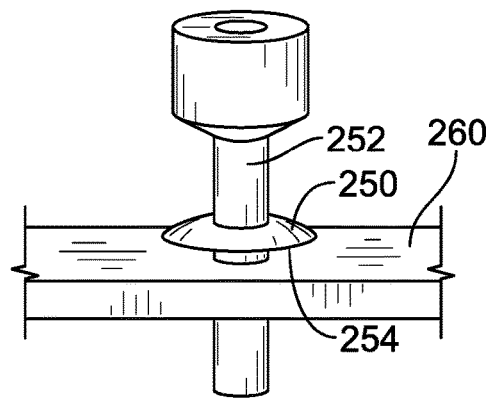
FIG. 14 is a side elevation view of a trocar inserted into a surgical site.

FIGS. 14-26 illustrate a method for closing a surgical site utilizing the instrument 140. Once the main critical portions of a minimally invasive surgical case are completed, the fascia must be closed (for trocars >8 mm). An arm 240 (either computer aided arm or hand-held disposable arm) is loaded with the first instrument 140. An appropriately sized guide ring 250 is attached to the trocar 252 and positioned with a lip 254 between the trocar 252 and the skin 260, as illustrated in FIG. 14.

Figure 15:
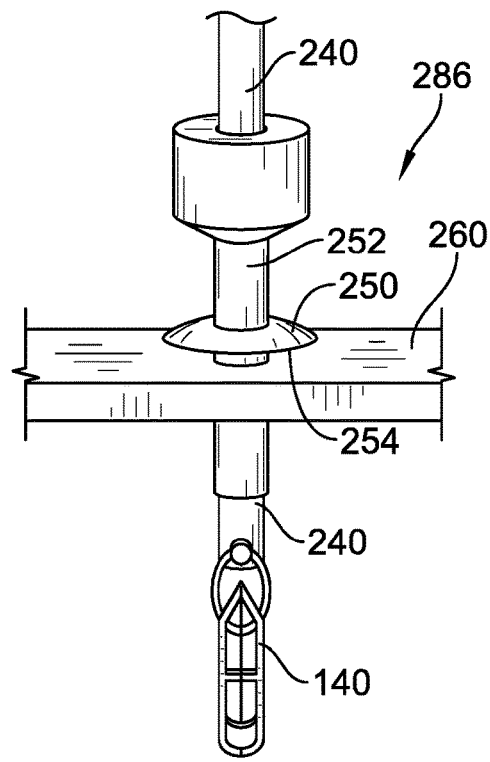
FIG. 15 is a side elevation view of the instrument shown in FIG. 4 inserted through the trocar.
Figure 16:
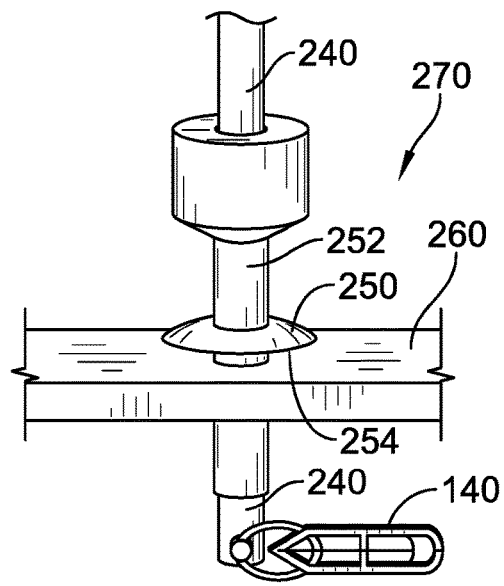
FIG. 16 is a side elevation view of the instrument rotated to a parallel configuration.
Figure 17:
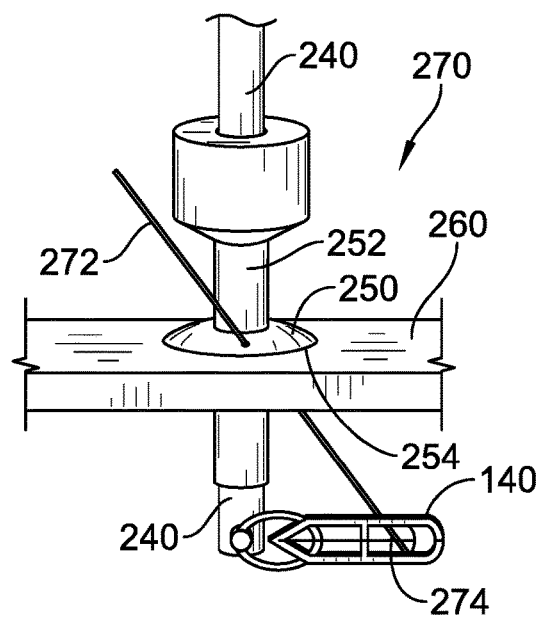
FIG. 17 is a side elevation view of a suture passer inserted through the guide ring and grabbing the suture in the instrument.

As illustrated in FIG. 15, the instrument 140 is advanced into the trocar 252 until full range of motion of the arm wrist is enabled. The instrument 140 is swiveled from a perpendicular position 286 to a parallel orientation in relation to the patient's fascial plane, as shown in FIG. 16. This can be done with automation if computer aided; or under direct control by the surgeon if using a disposable arm. Based on the size of defect being closed, the instrument 140 is rotated into a first suture position 270 in correspondence to the guide ring markings. A suture passer 272 is advanced through a correlating aperture 274 on the guide ring 250, as shown in FIG. 17. The suture passer 272 can be disposable or reusable. The suture passer 272 may have built in depth stops on the needle to prevent intra-abdominal injuries if passed by assistant. The suture passer 272 could be an external robotic arm and automated.

Figure 18:
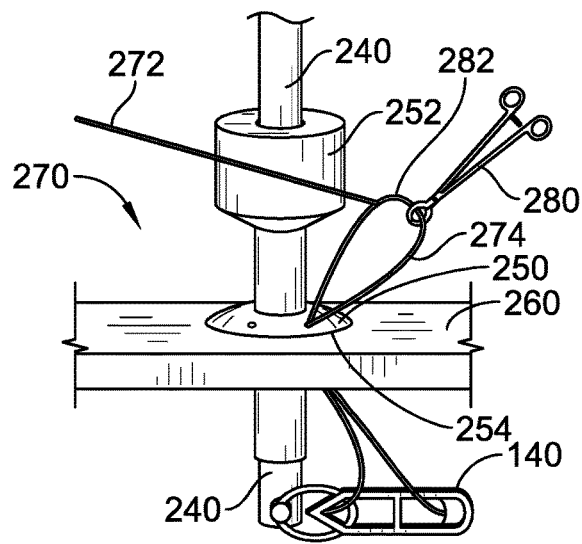
FIG. 18 is a side elevation view of the suture passer removing a segment of the suture from the surgical site.
Figure 19:
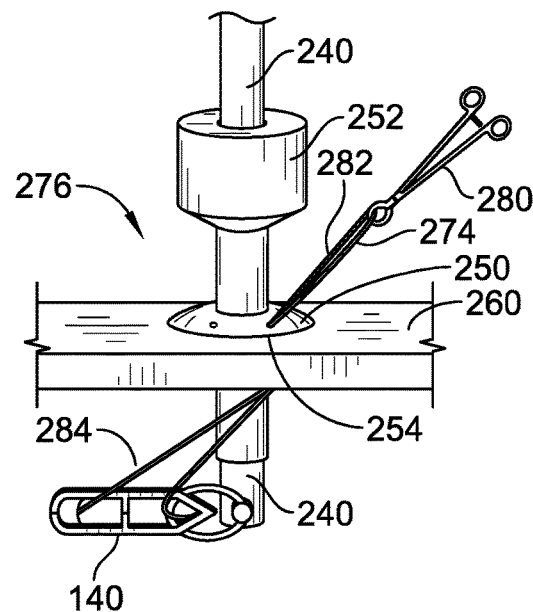
FIG. 19 is a side elevation view of the instrument rotated in the surgical site.
Figure 20:
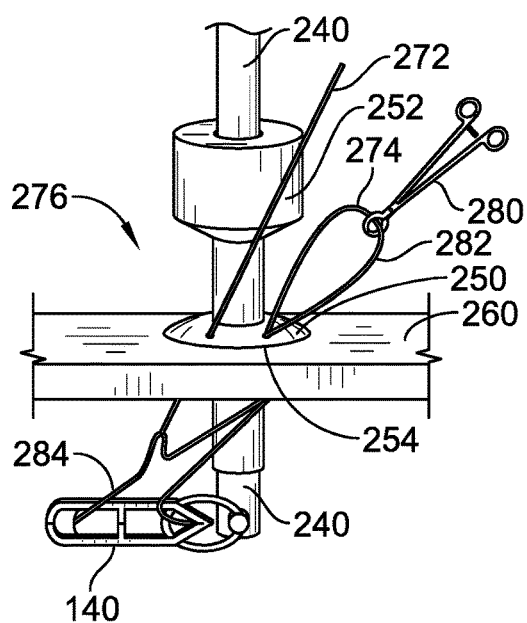
FIG. 20 is a side elevation view of the suture passer inserted through the guide ring and grabbing another segment of the suture.
Figure 21:
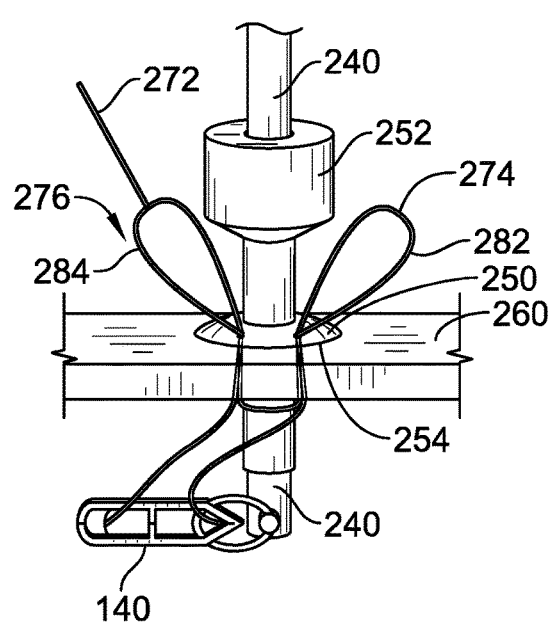
FIG. 21 is a side elevation view of the suture passer removing the other segment of the suture from the surgical site.
Figure 22:
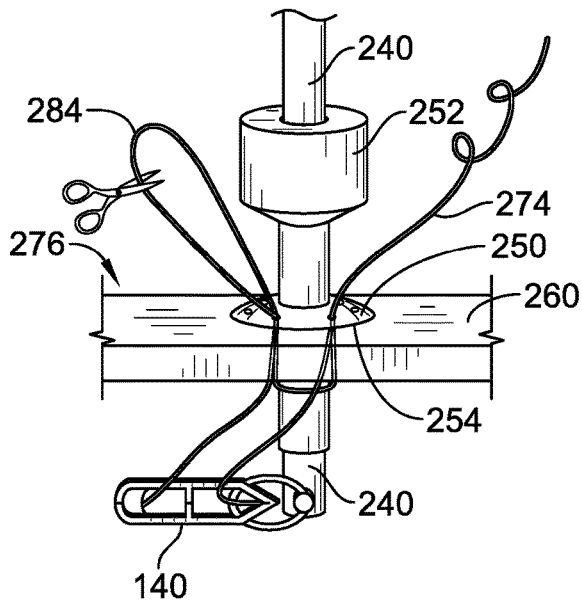
FIG. 22 is a side elevation view of the suture being cut.

The suture passer 272 enters the eyelets 162, 182 of the instrument 140 and secures a segment 278 of the suture 120 so that the segment 278 can be pulled out through the guide ring 250, as illustrated in FIG. 18. A clamp 280 is placed on the suture loop 288. In FIG. 19, the instrument 140 is rotated to a corresponding position 276 for a second throw. The suture passer 272 is advanced through a correlating aperture 282 on the guide ring 250, in FIG. 20. The suture passer 272 grasps another segment 284 of the suture 120 and pulls the segment 284 of the suture 120 back out through the correlating aperture 282 in the guide ring 250, in FIG. 21. The suture 120 is allowed to be completely pulled off of spool through the aperture. In FIG. 22, the loop of the suture 120 clamped. The suture 120 is then cut and held.

Figure 23:
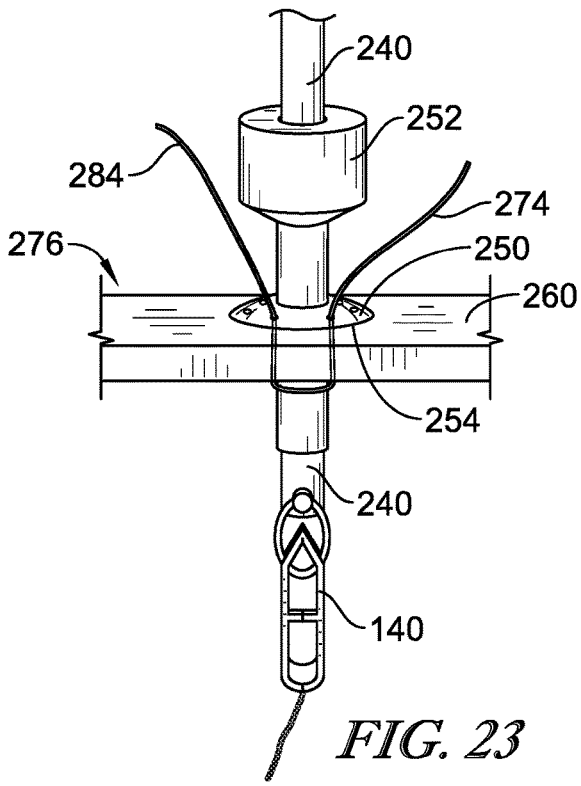
FIG. 23 is a side elevation view of the instrument rotated back to a perpendicular configuration.
Figure 24:
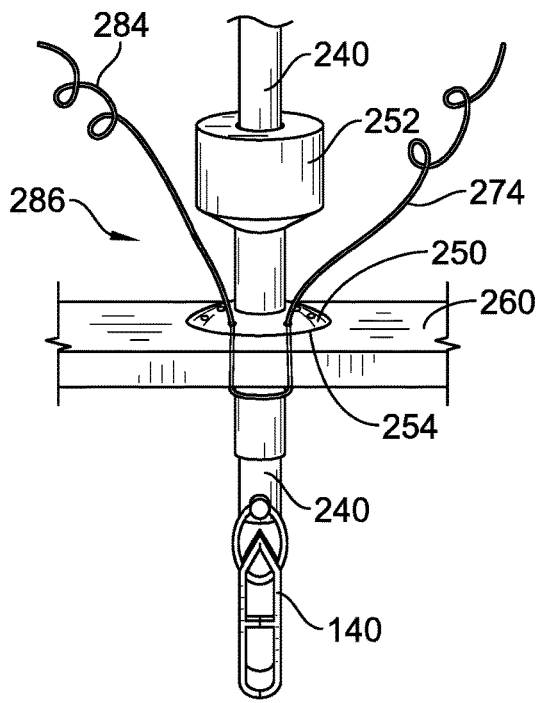
FIG. 24 is a side elevation view of the instrument being removed through the trocar.
Figure 25:
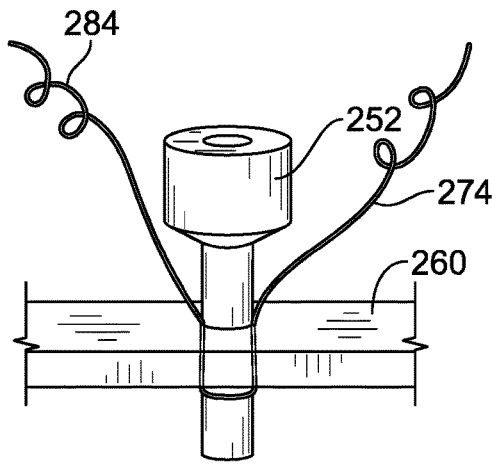
FIG. 25 is a side elevation view of the instrument and the arm removed from the trocar.
Figure 26:
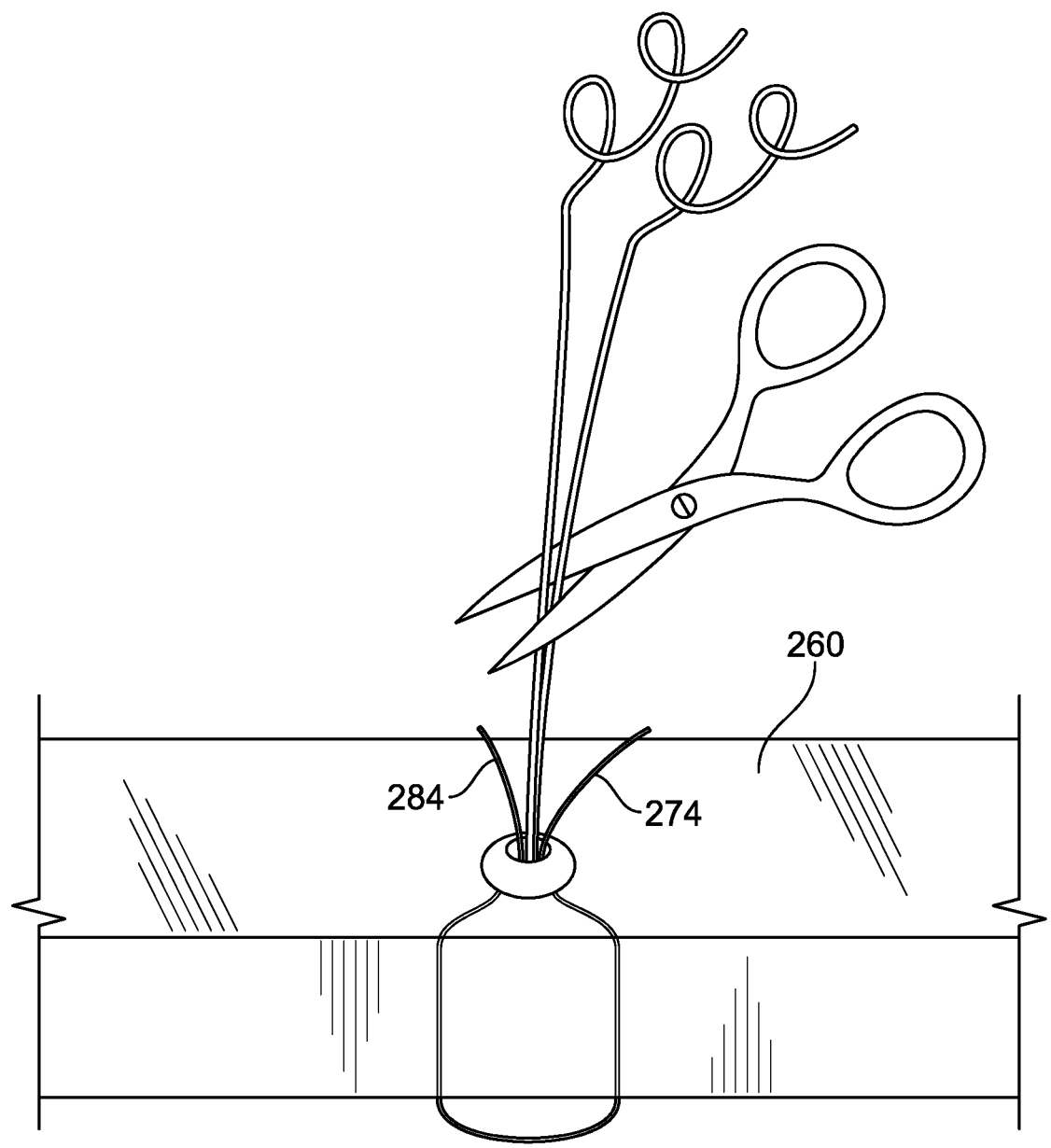
FIG. 26 is a side elevation view of the suture being tied to close the surgical site.
Figure 27:
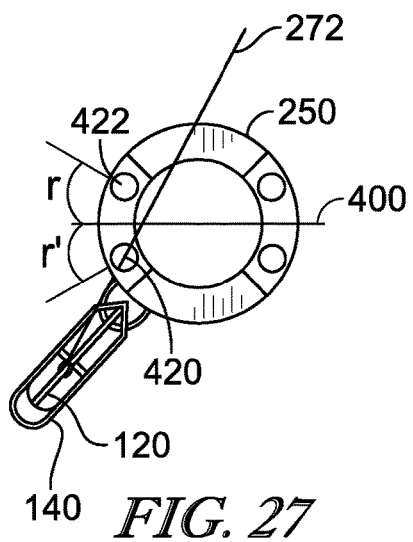
FIG. 27 is a top view of a suture grabber passed through a first aperture of the guide ring to pull a first half of a first suture through the guide ring.
Figure 28:
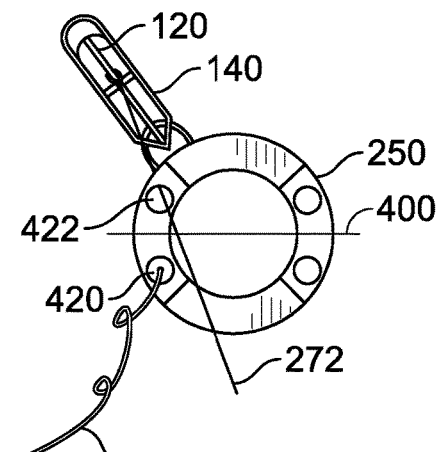
FIG. 28 is a top view of a suture grabber passed through a second aperture of the guide ring to pull a second half of the first suture through the guide ring.
Figure 29:
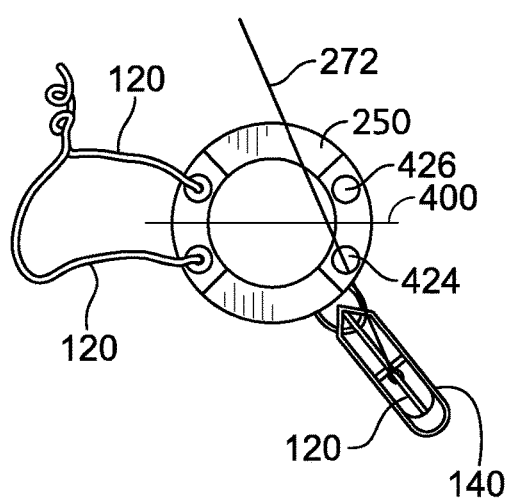
FIG. 29 is a top view of a suture grabber passed through a third aperture of the guide ring to pull a first half of a second suture through the guide ring.
Figure 30:
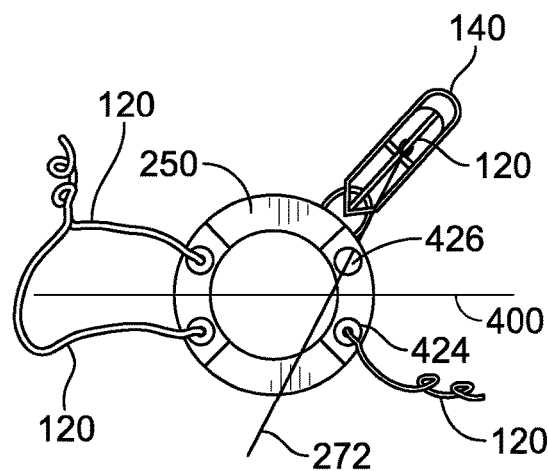
FIG. 30 is a top view of a suture grabber passed through a fourth aperture of the guide ring to pull a second half of the second suture through the guide ring.
Figure 31:
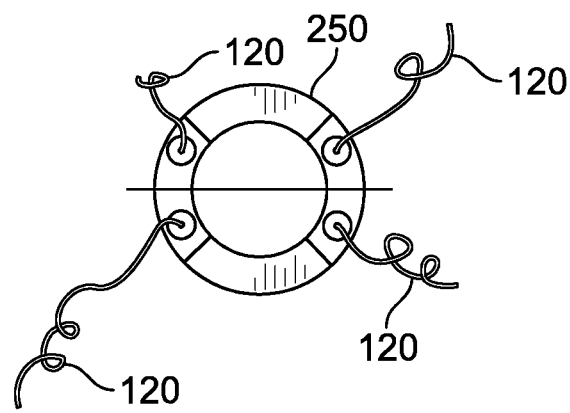
FIG. 31 is a top view of the incision with the first and second sutures prepared to be tied.
Figure 32:
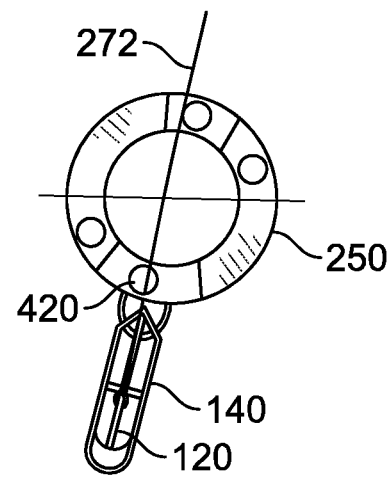
FIG. 32 is a top view of a suture grabber passed through the first aperture of the guide ring to pull a first half of a third suture through the guide ring.
Figure 33:
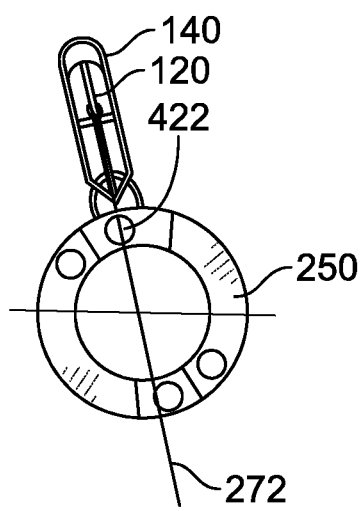
FIG. 33 is a top view of a suture grabber passed through the second aperture of the guide ring to pull a second half of the third suture through the guide ring.
Figure 34:
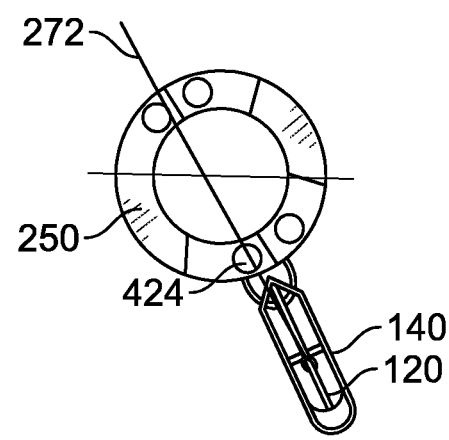
FIG. 34 is a top view of a suture grabber passed through the third aperture of the guide ring to pull a first half of a fourth suture through the guide ring.
Figure 35:
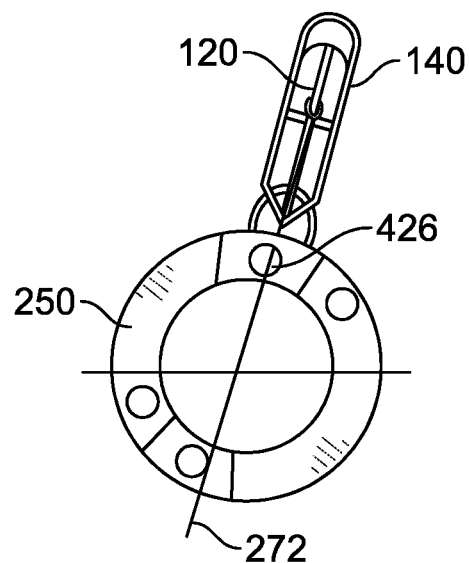
FIG. 35 is a top view of a suture grabber passed through the fourth aperture of the guide ring to pull a second half of the fourth suture through the guide ring.

In FIG. 23, the instrument 140 is rotated back to the perpendicular position 286. In FIGS. 24-25, the instrument 140 is removed from the surgical site. The guide ring 250, the arm 240, and the trocar 252 are removed and the suture 120 is tied using a surgeons knot in a normal fashion, as illustrated in FIG. 26. If the defect is larger, the process is repeated for each suture 120 until the desired number of sutures is placed. The sutures are always tied down after the trocar 252, the arm 240, and the guide ring 250 have been removed from the patient.

FIGS. 27-36 illustrate a method for utilizing the guide ring 250 during the procedure described above. The assembled guide ring 250 is placed around the laparoscopic trocar 252 at the end of the operation. The trocar aperture 320 is oriented distal to the abdominal cavity and the exit aperture 340 is oriented proximal to the abdominal cavity. The sidewall 304 of the guide ring 250 is thin and flexible yet strong enough to not be penetrated by the suture grabber 272. The sidewall 304 terminates in the exit aperture 340. The exit aperture 340, when in use, is placed below the dermis in the incision. The suture passer apertures 262 for the grabber 272 are located on the top end 300 of the guide ring 250 outside the skin. The exit aperture 340 is on the bottom end 302 of the guide ring 250. The grabber 272 passes out of the guide ring 250 through the exit aperture 340 between the trocar 252 and the bottom end 302. An axis of orientation 400 is the line of the interfaces of the hemi-guide rings 370. A gamma ($\gamma$) angle is the angle between the axis of orientation 400 and a line of orientation 402. A gamma prime ($\gamma'$) is the angle between the axis of orientation 400 and a line of orientation prime 404. The gamma ($\gamma$) and gamma prime ($\gamma'$) angles are equal.

Initially, the guide ring 250 is aligned with the axis of the line of orientation 400 in parallel with the incision. The guide ring 250 is aligned as to pass the grabber 272 through the fascia opposite to the side of the incision in which it was inserted. After the instrument 170 is inserted and parallel with the facia, the grabber 272 is inserted through an aperture 420 to retrieve suture 120. Once the suture 120 is secured, the grabber 272 is inserted into an aperture 422 and suture 120 is re-grasped and pulled through. The instrument 170 is then changed and the method is repeated for apertures 424 and 426 to form the suture configuration shown in FIG. 31.

Figure 36:
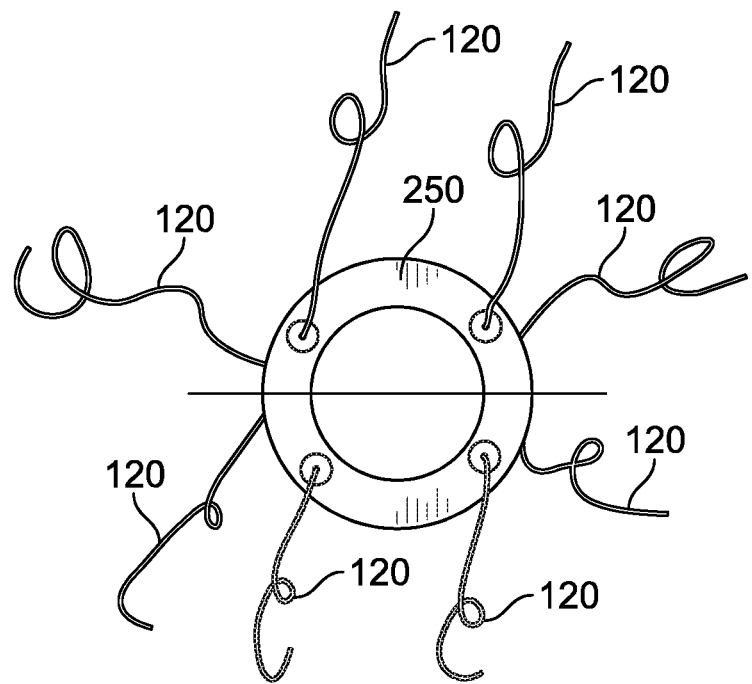
FIG. 36 is a top view of the incision with the first, second, third, and fourth sutures prepared to be tied.

Referring to FIGS. 32-36, for even larger size trocar closures (e.g. >16 mm), the guide ring 250 position is dynamic to facilitate positioning additional sutures 120 for fascial closure. The first two sutures 120 are passed through the fascia following the above sequence. A third instrument 170 is then inserted and aligned parallel with the facia. The same sequence of grabber 272 passes are again made; however, before each pass is made, the corresponding guide ring line of orientation 402 is lined up in parallel to the incision before the grabber 272 is passed into the corresponding apertures 420, 422, 424, 426 in the guide ring 250. Repeating this method for each of the aperture 420, 422, 424, 426 positions produces four sutures in the fascia, as illustrated in FIG. 36. The method can be extrapolated for even larger defects or used to create a woven pattern of suture 120.

The suture grabber 272 may be automated to move with the guide ring 250 and instrument 170 to optimize suture spacing. Alternatively, the suture grabber 272 could be oriented manually by the surgeon. The instrument 140 is compatible with a robotic arm (or a handheld device if a strictly laparoscopic case). The method can be automated and observed with direct surgeon vision and override control at a console. This allows the surgeon to tie the suture closure knot and close the skin once scrubbed in to close the patient. The instrument 140 can be used through the trocar it is closing without removal of the trocar.

The spool 110 is a pre-loaded swiveling internal spool of suture that eliminates the steps of loading suture and passing it through the abdominal wall. The suture on the spool may be manufactured with a needle for intra-abdominal suturing. The suture 120 is positioned reproducibly within the pertioneal cavity to ensure optimal suture spacing and tissue approximation leading to reduced incisional hernia rates in larger (>20 mm) laparoscopic defects. This allows single port site minimally invasive abdominal surgery to become more widespread and eventually the standard of care. Surgeons are able to guide an internal spool from the console while the bedside assistant can make safe, reliable passes under direct vision of the surgeon. Additionally, the guide ring 250 provides templates for optimal fascial suture spacing.

The instrument 140 is a disposable and there is potential for multiple suture passes in each instrument 140. Defects would require one instrument 140 per 6-10 mm in trocar diameter to optimize closure strength. The guide rings could be specifically manufactured for varying defect sizes. The instrument 140 can be scaled to fit varying sizes and brands of robotic arms. Spools can be preloaded and sold in varying package quantities.

The instrument 140 can be applied/modified to work in conjunction with current and future computer aided surgical devices. The instrument 140 allows the suture 120 to be within the peritoneal cavity. This offers a much simpler design and method for closing fascia on a widespread scale. The instrument 140 is adaptable for future use with surgical artificial intelligence. The instrument 140 can be used by all specialties that perform minimally invasive abdominal, thoracic or pelvic surgery. The instrument 140 can offer increased level of safety, precision, and ease of use.

In one aspect of the disclosed embodiments, a device for assisting in suturing the fascial tissue after an abdominal surgery is provided. The device includes a clam-shell housing that retains a spool of suture. The loose end of the suture is clamped and retained at an end of the device so that the suture extends through an eyelet between the end and the spool. The device is inserted into the abdomen through a surgical port. A suture grabber is inserted through a guide ring and grabs the suture in the eyelet of the device. The grabber pulls the suture through the fascial tissue to form a first end to be tied. The grabber than grabs another portion of the suture and pulls a second end to be tied through the fascial tissue. The device and port are removed and the two ends are tied.

In another aspect of the disclosed embodiments, a suturing device includes a clamshell body having a first side coupled to a second side by a hinge. The first side and the second side each have a clamping end opposite the hinge. A slot is formed in each of the first side and the second side. The slot in the first side is aligned with the slot in the second side when the clamshell body is closed to form a cavity. A spool is included having a rod extending from an end cap. The end cap is retained in the cavity and is rotatable relative to the clamshell body. A suture is wound around the rod of the spool. The clamping ends of the first side and the second side lock together to capture an end of the suture.

In some embodiments, each of the first side and the second side may include a first slot and a second slot. The first slots of the first side and the second side may form a first cavity to retain a first end cap of the spool. The second slots of the first side and the second side may form a second cavity to retain a second end cap of the spool. The rod of the spool may extend between the first end cap and the second end cap.

In some embodiments, an eyelet may extend between the ends of the first side. The suture may be accessible through the eyelet. An eyelet may extend between the ends of the second side. The suture may be accessible through the eyelet. An eyelet may be formed between the first side and the second side when the first side and the second side are coupled together. The suture may be accessible through the eyelet.

In some embodiments, the suture may extend between the spool and the clamping end of the clamshell body. The clamshell body may be configured to be retained by a robotic arm. The clamshell body may be sized to be extended through a trocar.

In some embodiments, a guide ring may be configured to couple to a trocar. The guide ring may be configured to receive a suture grabber that grabs the suture in the clamshell body. The guide ring may include a conical sidewall extending between a first end and a second end. The conical sidewall may be sized to position around a trocar. The first end of the guide ring may include a flange having a plurality of openings. The openings may be sized to receive a suture grabber. An opening defined by the flange may be sized to position around a trocar. The guide ring may include a first half and a second half that is separable from the first half. The first half may be coupled to the second half to couple the guide ring to the trocar. A needle may be attached to an end of the suture for a hernia closure procedure.

In yet another aspect of the disclosed embodiments, a method of suturing an abdominal cavity includes inserting a spool of suture in the abdominal cavity. The method also includes capturing a first portion of the suture and removing the first portion from the abdominal cavity. The method also includes capturing a second portion of the suture and removing the second portion from the abdominal cavity. The method also includes tying the first portion to the second portion outside of the abdominal cavity.

In some embodiments, the spool may be retained in a clamshell body. The method may also include inserting the clamshell body into the abdominal cavity. The method may also include capturing the first portion of the suture in an eyelet of the clamshell body. The method may also include capturing the second portion of the suture in the eyelet of the clamshell body. The method may also include capturing the first portion of the suture and the second portion of the suture with a suture grabber. The method may also include inserting the suture grabber through an opening of a guide ring.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless cannot be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles can have been presented, they need not be utilized in combination, and many combinations of aspects and principles are possible in light of the various embodiments provided above.

The invention claimed is:

1. A suturing device comprising:
   a clamshell body having a first side coupled to a second side by a hinge, the first side and the second side each having a clamping end opposite the hinge;
   a slot formed in each of the first side and the second side, the slot in the first side being aligned with the slot in the second side when the clamshell body is closed to form a cavity;
   a spool having a rod extending from an end cap, the end cap retained in the cavity and rotatable relative to the clamshell body; and
   a suture wound around the rod of the spool,
   wherein the clamping ends of the first side and the second side lock together and capture an end of the suture in a fixed position between the clamping ends.

2. The device of claim 1, wherein the slot formed in each of the first side and the second side is a first slot and the cavity is a first cavity that retains a first end cap of the spool, and
   a second slot of the first side and a second slot of the second side form a second cavity to retain a second end cap of the spool when the clamshell body is closed.

3. The device of claim 2, wherein the rod of the spool extends between the first end cap and the second end cap.

4. The device of claim 1, wherein the clamshell body includes an eyelet between the ends of the first side, the suture being accessible through the eyelet.

5. The device of claim 1, wherein the clamshell body includes an eyelet between the ends of the second side, the suture being accessible through the eyelet.

6. The device of claim 1, wherein the clamshell body includes an eyelet formed between the first side and the second side when the first side and the second side are coupled together, the suture being accessible through the eyelet.

7. The device of claim 1, wherein the suture extends between the spool and the clamping end of the clamshell body.

8. The device of claim 1, wherein the clamshell body is configured to be retained by a robotic arm.

9. The device of claim 1, wherein the clamshell body is sized to be extended through a trocar.

10. The device of claim 1, further comprising a guide ring that is configured to couple to a trocar, the guide ring body configured to receive a suture grabber that grabs the suture in the clamshell body.

11. The device of claim 10, wherein the guide ring includes a conical sidewall extending between a first end and a second end, the conical sidewall sized to position around a trocar.

12. The device of claim 11, wherein the first end of the guide ring includes a flange having a plurality of openings, the openings being sized to receive a suture grabber.

13. The device of claim 12, including an opening defined by the flange, the opening sized to position around a trocar.

14. The device of claim 1, further comprising a needle attached to an end of the suture for a hernia closure procedure.

* * * * *